United States Patent [19]

Dean et al.

[11] Patent Number: 5,053,503

[45] Date of Patent: Oct. 1, 1991

[54] CHELATING AGENTS

[75] Inventors: Richard T. Dean; Robert W. Weber, both of Downingtown, Pa.

[73] Assignee: Centocor, Malvern, Pa.

[21] Appl. No.: 312,767

[22] Filed: Feb. 17, 1989

[51] Int. Cl.$^5$ .......................................... C07D 251/02
[52] U.S. Cl. ................................................... 540/474
[58] Field of Search ....................................... 540/474

[56] References Cited

U.S. PATENT DOCUMENTS

| | | | |
|---|---|---|---|
| 4,174,428 | 11/1979 | Kobuke | 540/474 |
| 4,432,907 | 2/1984 | Wieder et al. | 436/500 |
| 4,472,509 | 9/1984 | Gansow et al. | 436/548 |
| 4,659,839 | 4/1987 | Micolotti et al. | 548/546 |
| 4,671,958 | 7/1987 | Rodwell et al. | 514/2 |

FOREIGN PATENT DOCUMENTS

| | | |
|---|---|---|
| 0173629 | 8/1985 | European Pat. Off. . |
| 0188256 | 7/1986 | European Pat. Off. . |
| 0232751 | 8/1987 | European Pat. Off. ............ 540/474 |
| 89/01476 | 2/1989 | PCT Int'l Appl. . |

OTHER PUBLICATIONS

Khaw, et al, *Science*, 209, 295 (1980).
Krejcarek, et al, *Biochem. Biophys. Res. Comm.*, 77, 581 (1977).
Childs, R. L. and Hnatowich, D. J., *J. Nuc. Med.*, 26, 293 (1985).
Stetter, H. and Frank, W., *Angew. Chem. Int. Ed. Engl.*, 15, 686 (1976).
Desreux, J. F., Loncin, M. F., and Merciny, E., *Inorg. Chem.*, 25, 2646 (1986).
Meares, C. F., Moi, M. K. and De Nardo, S. J., *J. Am. Chem. Soc.*, 110, 6266 (1988).
Tweedle, M. F., et al, *J. Nuc. Med.*, 28, 705 (1988).
Paik, C. H., et al, *J. Nuc. Med.*, 27, 959 (1986).
Paik, C. H., et al, *J. Nuc. Med.*, 28, 572 (1987).
Paik, C. H., et al, *J. Nuc. Med.*, 29, 889 (1988).
Meares, C. F., et al, *Eur. J. Nuc. Med.*, 12, 455 (1986).
Meares, C. F., et al, *Int. J. Cancer Supp.*, 2, 99 (1988).
Parker, et al., *Pure & Appl. Chem.*, vol. 61, No. 9, 1637–1641 (1989).
Craig, et al., *J. Chem. Soc., Chem. Commun.*, (1989), pp. 794–796.
Cox, et al., *J. Chem. Soc., Chem. Commun.*, (1989), pp. 797–798.
Paik, et al., *J. Nucl. Sci.*, vol. 30, No. 10, p. 1693 (Oct. 1989).
Paik, et al., *Nucl. Med. Biol.*, vol. 16, No. 5, pp. 475–481 (1989).
Shrikant, et al., *Nucl. Med. Biol.*, vol. 16, No. 6, pp. 587–597 (1989).

*Primary Examiner*—David B. Springer
*Attorney, Agent, or Firm*—Woodcock Washburn Kurtz Mackiewicz & Norris

[57] ABSTRACT

A bifunctional chelating agent for joining an antibody or antibody fragment and a metallic radionuclide is disclosed. The agent consists of a derivative of 1,4,7,10-tetraazacyclododecane-1,4,7-triacetic acid or a 1,4,7,10-tetraazacyclododecane-1,4,7,10-tetraacetic acid, an organic linking radical which optionally contains a cleavable group, and a function capable of reacting with a site on a protein. Radiodiagnostic or radiotherapeutic precursors comprising an antibody or antibody fragment and the above-described bifunctional chelating agent and radiodiagnostic or radiotherapeutic agent comprising a metallic radionuclide and the above mentioned precursor are also disclosed.

23 Claims, No Drawings

CHELATING AGENTS

BACKGROUND OF THE INVENTION

1. Field of the Invention

This invention relates to the field of radiolabeled proteins for diagnostic and therapeutic applications and, more particularly, to chelating agents useful for coupling metal ions to biologically active molecules.

2. Background of the Invention

The attachment of radiometals to proteins, especially antibodies and antibody fragments results in the formation of new radiodiagnostic and radiotherapeutic agents. The use of pure, homogeneous monoclonal antibodies for this purpose has been recognized as an important advancement in nuclear medicine.

The performance of the radiometal-protein conjugates depends on a number of factors, including the stability of the metal chelate complex in regard to loss of the radiometal from the chelate in vivo and the ability of the conjugates to localize to the target tissue. As it is desired that the radioactive agent not accumulate in any but the target tissues, the performance of such agents also depends on the extent and rate at which the agents are eventually cleared from non-target tissue.

Monoclonal antibodies are highly specific and can be used as vehicles to deliver substances to specific target sites. Numerous antibodies have been developed with affinity for targets such as myosin, fibrinogen, atherosclerotic tissue and tumors, to name just a few, and work in this area continues.

Radiometals may be attached to proteins and antibodies through the use of bifunctional chelating agents. The bifunctional agent is selected such that it is capable of binding radiometals by chelation as well as forming a linkage to the protein. For example, diethylenetriamine pentaacetic acid (DTPA) has been conjugated to an antimyosin antibody, and the proteinbound DTPA used to chelate In-111 (Khaw, et al., *Science*, 209, 295 (1980), See also Krejcarek, et al., *Biochem. Biophys. Res. Comm.*, 77, 581 (1977) and Childs, R. L. and Hnatowich, D. J., *J. Nuc. Med.*, 26, 293 (1985)).

The stability of the metal-chelator complex is important, as leakage of the radiometal from the protein-chelate conjugate can result in a high background during imaging procedures and damage to non-targeted tissues in radioimmunotherapy. U.S. Pat. No. 4,472,509 discloses bifunctional DTPA derivatives which form metal complexes with increased in vivo stability. The ligand 1,4,7,10-tetraazacyclododecane-1,4,7,10-tetraacetic acid, forms remarkably stable complexes with a number of metals, (Stetter, H. and Frank, W., *Angew. Chem. Int Ed. Engl.*, 15, 686, (1976), Desreux, J. F., Loncin, M. F., and Merciny, E., *Inorg. Chem.* 25, 2646 (1986)). The 2-(p-nitrobenzyl) derivative of DOTA has been described (Meares, C. F., Moi, M. K. and De Nardo, S.J., *J. Am. Chem. Soc.* 110, 6266 (1988)) and the yttrium complex was determined to be inert to loss of the metal from the complex to serum proteins. A series of 1-substituted analogs of DOTA have been described (Tweedle, M. F. et. al., Eur. Pat. Appl. EP 232, 751). The gadolinium complex of one such analog, 1,4,7,10-tetraazacyclododecane-1,4,7-triacetic acid, was reported to be inert to reaction with endogenously available ions (Tweedle, M. F. et al., *J. Nuc. Med.*, 28, 705 (1988)).

Bifunctional chelators have been coupled to proteins and antibodies at a number of chemical sites. Lysyl side chain amino groups have been modified (EPO Publication No. 188, 256) and chelators have been site-selectively attached to oxidized antibody carbohydrate moieties (U.S. Pat. No. 4,671,958). Chelators have also been attached by reaction with free sulfhydryl groups (U.S. Pat. No. 4,659,839, U.S. Pat. No. 4,671,958, EPO Publication No. 173, 629 and U.S. application Ser. No. 199,931). Site-selective antibody modification is advantageous as the chelator may be placed at points removed from the antigen-binding region thus preserving the immunoreactivity of the protein.

The accumulation of radiolabeled antibodies in non-target tissue is a factor which limits the dosage at which the conjugates may be used. The clearance of radio metal labeled antibodies by the use of a cleavable bifunctional chelating agent has been addressed. DTPA derivatives containing cleavable functionalities have been used to form conjugates between indium-111 and antibodies (Park, C. H. et al., *J. Nuc. Med.*, 27, 959 (1986), 28, 572 (1987), 29, 889 (1988), Meares, C. F., et al., *Eur. J. Nuc. Med.*, 12, 455 (1986), Meares., C. F., et al., *Int. J. Cancer* Supp. 2, 99 (1988)). In general, these compositions showed an increased clearance rate in mice.

A need for bifunctional chelating agents which are capable of forming stable metal complexes, and optionally which contain a cleavable linking unit, continues to exist in the field of nuclear medicine.

SUMMARY OF THE INVENTION

The present invention provides a bifunctional chelating agent for joining an antibody or antibody fragment and a metallic radionuclide. The agent consists of a derivative of 1,4,7,10-tetraazacyclododecane-1,4,7-triacetic acid (hereinafter "D03A") or a 1,4,7,10-tetraazacyclododecane-1,4,7,10-tetraacetic acid (hereinafter "DOTA"), an organic linking radical which optionally contains a cleavable group, and a function capable of reacting with a site on a protein. This invention further relates to a radiodiagnostic or radiotherapeutic precursor comprising an antibody or antibody fragment having the above-described bifunctional chelating agent bound to it, and to a radiodiagnostic or radiotherapeutic agent comprising a metallic radionuclide bound to said precursor. Still further, this invention relates to a method of preparing the novel bifunctional chelating agents and to novel precursors for use in said process.

DETAILED DESCRIPTION OF THE INVENTION

The bifunctional chelating agents of this invention are advantageous for a number of reasons. First, the present D03A and DOTA chelators provide metal complexes of high stability, thereby reducing the incidence of background during imaging procedures or damage to non-targeted tissues in radioimmunotherapy. A second advantage of the claimed coupling agents arises from the preferable inclusion of a cleavable group in the organic linking radical portion of the molecule. The presence of this cleavable group should result in decreased accumulation of radiolabeled protein in tissues other than those which comprise specific binding sites of the protein. Another advantage of the claimed coupling agents results from the preferable incorporation of functional groups in the agents capable of reacting with free sulfhydryl sites on biologically functional proteins such as antibodies. When attached to these sites, the radionuclide chelator is removed from the antigen binding region at that antibody, thus reducing the likelihood of interference of the chelator with antibody-antigen binding.

The coupling agents of this invention may be represented by the following formulas:

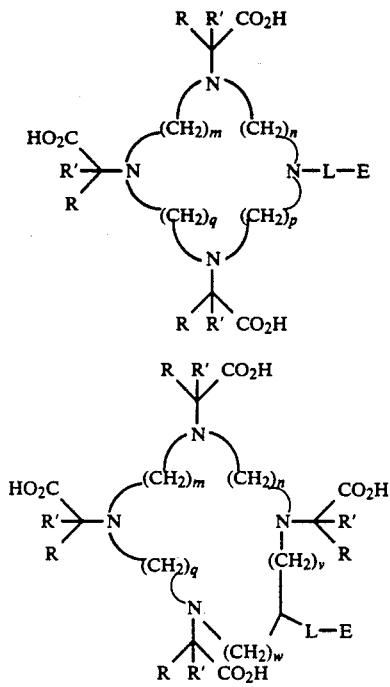

wherein E is a group capable of reacting with a site on the protein; L is an organic linking radical which may contain a cleavable site; R and R' are independently hydrogen or lower alkyl; m, n, p and q are integers which are independently selected from the group consisting of 2 and 3; v and w are integers which are independently selected the group consisting of 0, 1, and 2. The term "alkyl" as used herein includes branched and straight chain alkyl groups.

In the agent of the invention, E may be a sulfhydryl selective electrophile including those in the group of haloalkyl, sulfonate ester, maleimide and aziridine. Preferably, the sulfhydryl electrophile is selected from the group consisting of $ClCH_2CONH-$, $BrCH_2CONH-$, $ICH_2CONH-$, and N-substituted maleimide. E may also be an amine capable of reacting with antibody carboxyls or oxidized carbohydrate. In addition, E may be a group which can react with antibody amino groups such as active esters.

The organic linking radical L has at least two valencies for joining the electrophilic moiety E and the chelating moiety C. Suitable organic linking radicals L may be selected from the group consisting of optionally substituted alkyl, optionally substituted alkyl containing heteroatom substitutes for carbon (e.g., in which a carbon in the aliphatic chain is replaced with a heteroatom such as N, O or S), and optionally substituted aryl groups. The term "alkyl" as used herein indicates a straight alkyl chain of from 1 to 12 carbons which may be optionally substituted with additional carbons. The term "optionally substituted" as used herein refers to optional substitution with functional groups such as but not limited to alkyl groups, aryl groups, alkoxy groups, hydroxy groups, and carboxy groups, which will not interfere with the desired coupling and labeling reactions.

The organic linking radical preferably contains one or more cleavable sites, thus enhancing clearance of the radiometal from non-target tissue. As used herein, the expression "cleavable site" refers to a chemical bond in the linking radical, the breaking of which bond serves to dissociate the radiometal in chelated form from the labelled protein, which bond has an appreciable rate of dissociation by metabolism in an organ. Such dissociation should preferably occur at a rate of at least about 50% within the half-life of the radiometal.

The cleavable site can be part of the organic linking radical or can form one of the bonds joining the organic linking radical to the chelating moiety and/or the electrophilic moiety. Most preferably, the cleavable site is an alkyl or aryl ester, an ester of an aryl alcohol or an aryl ester of an alkyl alcohol. Preferred organic linking radicals containing cleavable sites are selected from those of the formula:

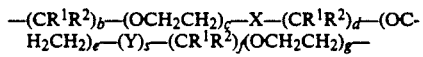

wherein each $R^1$ and $R^2$ is independently selected from the group consisting of hydrogen, lower alkyl, carboxyl, hydroxyalkyl and alkoxyalkyl; b is an integer of from 0 to 12 inclusive, c is an integer of from 0 to 5 inclusive, X is selected from the group consisting of $-COO-$, $-CONR^3-$ or $-COS-$, $-OCH_2COO-$, $-OOC-$, $-R^3NOC-$, $-SOC-$, $-OOCCH_2O-$, $-OAr-$ and $-ArO-$; Ar represents an moiety; $R^3$ is hydrogen or lower alkyl; d, e, f and g are independently integers from 0 to 5 inclusive; s is 0 or 1; Y is selected from the same group as X, provided that when X is $-CONR^3-$, or $-R^3NOC-$, then s is 1 and Y is $-COO-$, $-COS-$, $-OCH_2COO-$, $-OOC-$, $-SOC-$, $-OOCCH_2O-$, $-OAr-$ or $-ArO-$. An example of such a cleavable linking radical is $-(CH_2)_5CO_2CH_2CH_2OCH_2CH_2-$.

Preferred organic linking radicals which do not contain cleavable sites may be represented by the formula:

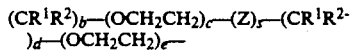

wherein each $R^1$ and $R^2$ is independently selected from the group consisting of hydrogen, lower alkyl, carboxyl, hydroxyalkyl and alkoxyalkyl; b is an integer of from 0 to 12 inclusive; c, d and e are independently integers of from 0 to 5 inclusive; Z is selected from the group consisting of $-CONR^3-$, $-R^3NOC-$, and $-Ar-$; $R^3$ is hydrogen or lower alkyl; Ar is an aromatic moiety; and s is 0 or 1. Examples of such linking radicals include

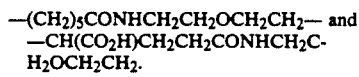

The bifunctional coupling agents of the invention are useful for binding an antibody or antibody fragment with metallic radionuclides such as but not limited to isotopes of In, Ga and Y. The bifunctional coupling agents can be used to selectively attach a radionuclide to a sulfhydryl-containing group on a protein and are thus useful for the preparation of compositions of the formula Ab-S-E-L-C-M, wherein Ab is an antibody or fragment derived therefrom, S is a sulfhydryl, M is a radiometal, and E and L are as defined above, and C is the chelator.

Sulfhydryls on proteins are due to the presence of cysteine residues and may be modified under conditions which leave other amino acids and functionalities in the protein unmodified. For biologically functional proteins, such as antibodies, modification at a free sulfhydryl is usually distal to the antigen binding sites.

Proteins containing a free sulfhydryl group can be conjugated directly to the bifunctional coupling agent. Many proteins do not possess sulfhydryl groups but do contain disulfide bonds as cystine amino acids. These disulfide bonds can be reduced to free cysteines by mild reducing agents. Among suitable reducing agents are dithiothreitol, dithioerythritol, cysteine, mercaptoethanol or a variety of other reducing agents. Optimal use of invention includes the purification of the reduced protein. This purification can be achieved by standard methods, usually by gel filtration chromatography. A representative reduction would be addition of sufficient dithiothreitol to give a 2-20 mM concentration, addition being to a 1-10 mg/mL solution of protein in a buffer at pH 7 to 8. After approximately one hour the protein is passed down a gel filtration column in the buffer desired for reaction with the bifunctional coupling reagent.

In a preferred embodiment, the bifunctional coupling agent is employed to join a radionuclide and an antibody molecule or fragment. Intact antibodies do not normally possess free cysteine, but do contain cystine disulfides. An intact antibody can therefore be joined to the bifunctional coupling agent after reduction as described above. Intact antibodies can also be treated with a proteolytic enzyme, such as pepsin, to give an antigen binding fragment F(ab')$_2$ and another fragment F$_c$. The F(ab')$_2$ can be split into two Fab' fragments by mild reduction as described above. This Fab' contains both an antigen binding site as well as free cysteine thiol groups. The antigen binding properties of the Fab' are unaffected by reaction with the bifunctional reagent, as the section of the protein comprising the antigen binding site does not react with the bifunctional reagent.

The bifunctional coupling agent is added to the protein solution in an excess relative to the number of free sulfhydryls to prepare a radiodiagnostic or radiotherapeutic precursor. Typically to a 1-2 mg/mL solution of protein in a buffer at pH 7 to 8, preferably pH 7.0, is added the bifunctional coupling agent in a co-solvent such as dimethylsulfoxide or dimethylformamide, if required. The agent is present in a 5-30 molar ratio to the number of sulfhydryl groups. If a co-solvent is necessary to solubilize the agent, the concentration of the co-solvent is kept between 1 and 15% v/v, usually around 5%. A reaction time of 1 to 2 hours is generally sufficient to react all of the sulfhydryls present, longer reaction times than this are not optimal. Excess bifunctional coupling agent is then removed. Usually this is accomplished using gel filtration chromatography.

The protein-coupling agent conjugate may be complexed with a radiometal, to form radiodiagnostic or radiotherapeutic agents, by mixing the modified protein with a salt of the radiometal in a suitably buffered solution. The In-111 complex of the bifunctional coupling agent can be prepared in this fashion by mixing In-111 chloride with the protein conjugate in citrate buffer at pH 5. The mixture is allowed to sit at or near ambient temperature until more than 90 and usually more than 95% of the indium becomes attached to the protein. This can be determined by several techniques including gel filtration HPLC and thin layer chromatography methods.

Examples of preferred coupling agents within the scope of this invention are set forth in the following Table.

| TABLE OF COMPOUNDS | | |
|---|---|---|
| C | L | E |
| [cyclen-tetraacetic acid structure with CO$_2$H groups] | [hexanoyl-NH-CH$_2$CH$_2$-O-CH$_2$CH$_3$] | NHCOCH$_2$Br |
| " | [hexanoate ester -O-CH$_2$CH$_2$-O-CH$_2$CH$_3$] | " |
| " | [CO$_2$H-substituted amide -C(O)NH-CH$_2$CH$_2$-O-CH$_2$CH$_3$] | [maleimide] |
| " | [CO$_2$H-substituted ester -C(O)O-CH$_2$CH$_2$-O-CH$_2$CH$_3$] | " |

-continued

TABLE OF COMPOUNDS

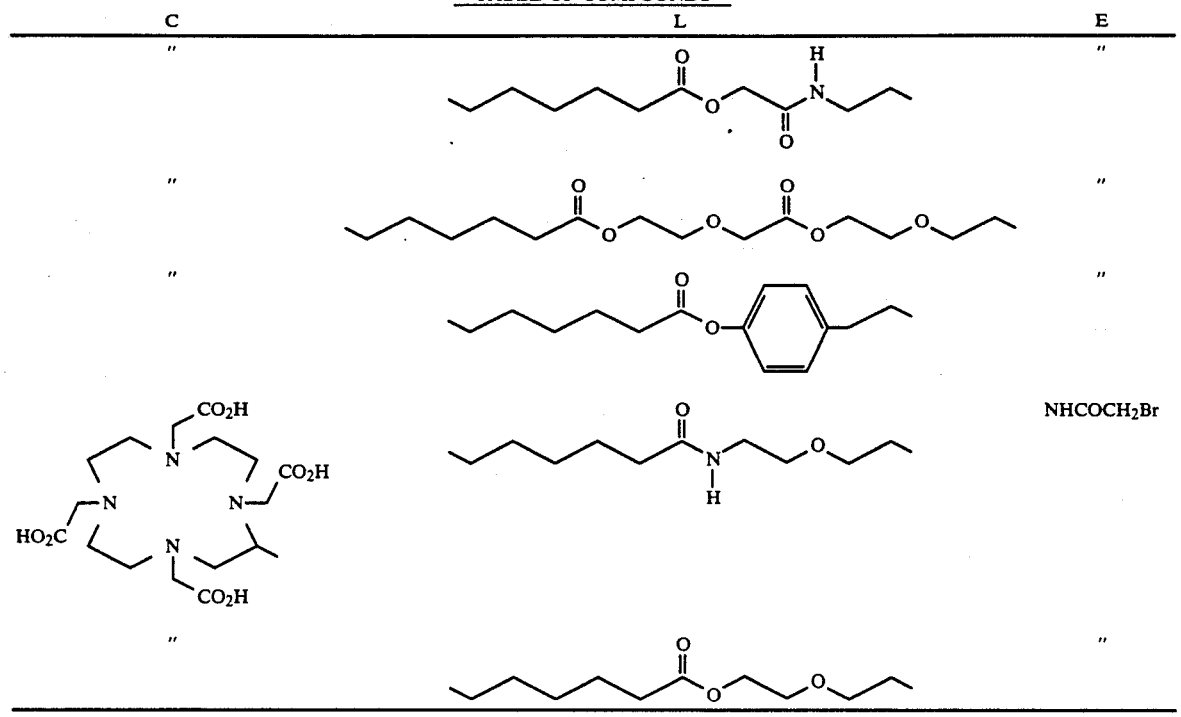

The following are examples of specifically preferred bifunctional chelating agents of the invention.

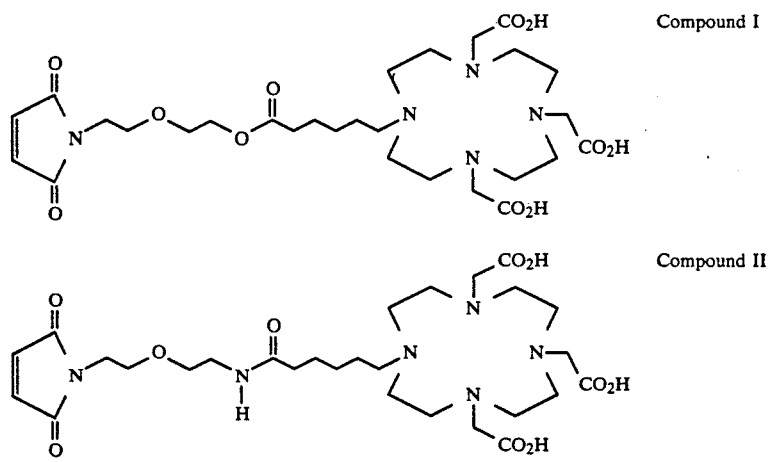

The coupling agents of the invention can be prepared by hydrolysis of novel precursors of the formulas

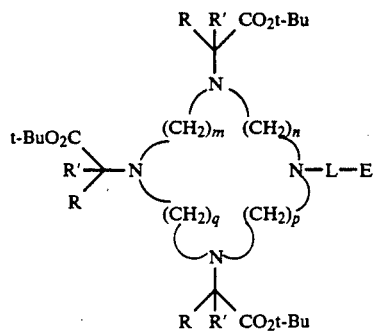

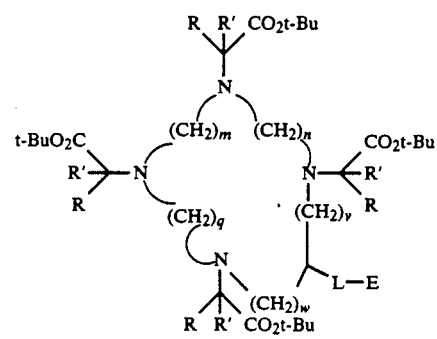

Schemes A and B below illustrate the preparation of novel precursors and coupling agents of this invention. These processes are described in more detail in Examples 1 and 2 for the preparation of 1-(6-(5-maleimido-3- oxapentyloxy)-6-oxohexyl)-1,4,7,10,-tetraazacyclododecane-4,7,10-triacetic acid (Compound I) and 1-(6-oxo-7-aza-10-oxa-12-(1-maleimido)dodecyl)1,4,7,10-tetraazacyclododecane-4,7,10-triacetic acid (Compound II).
Compound I can be readily prepared according to Scheme A below:
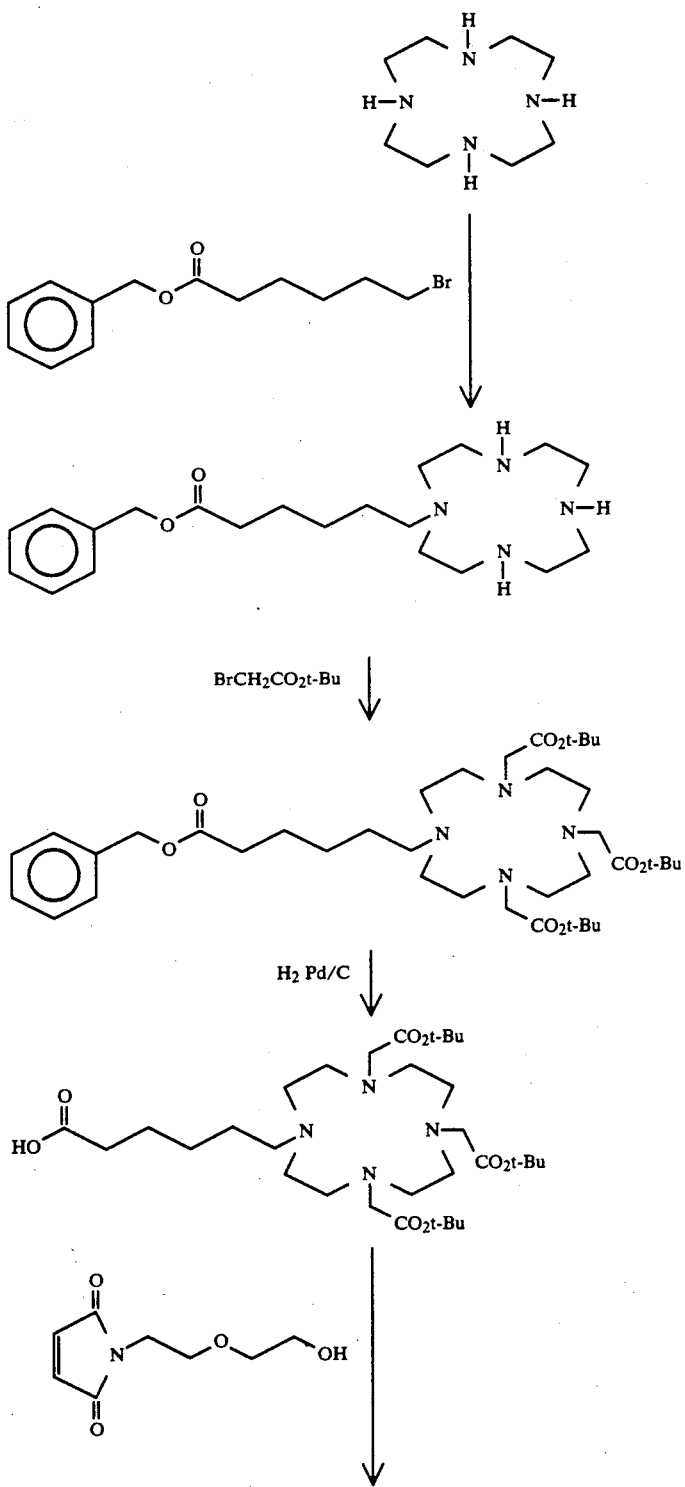

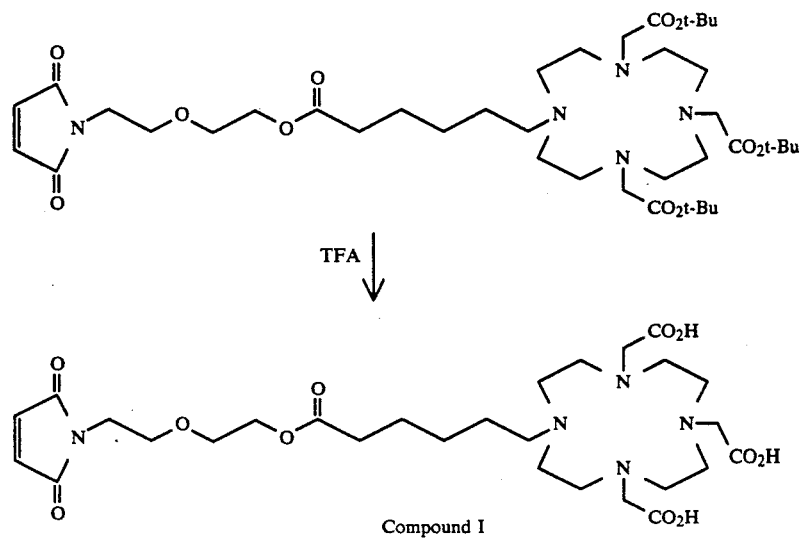
Compound II can be readily prepared according to Scheme B below:
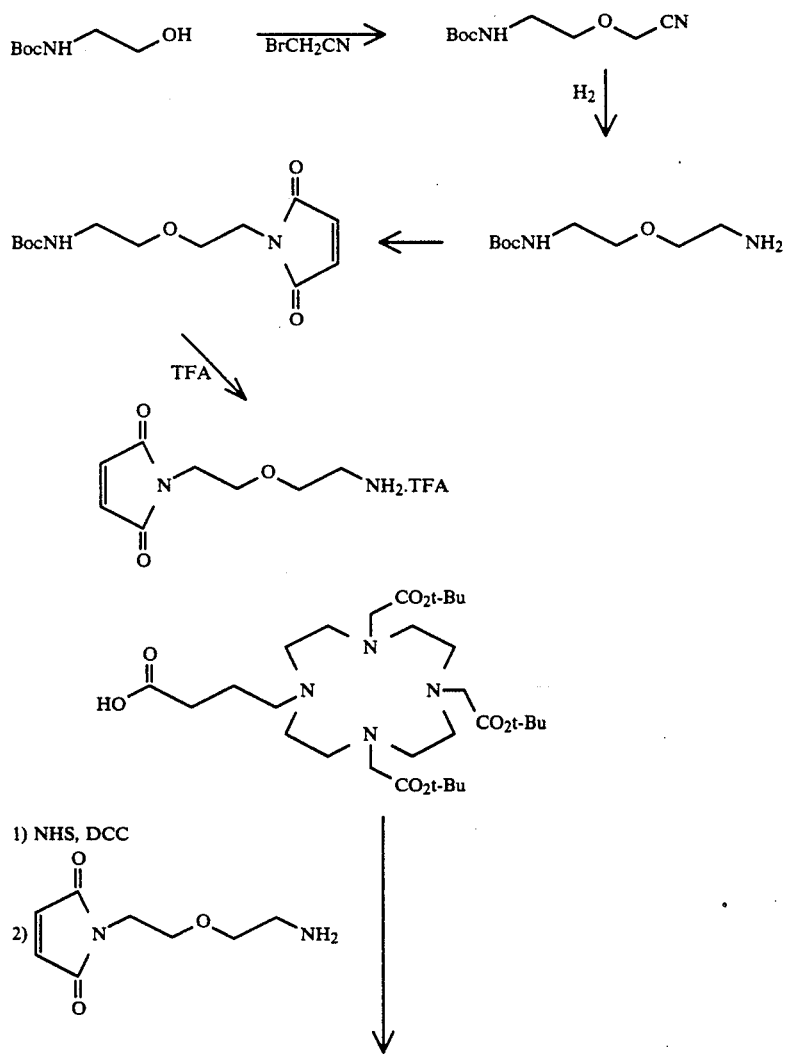

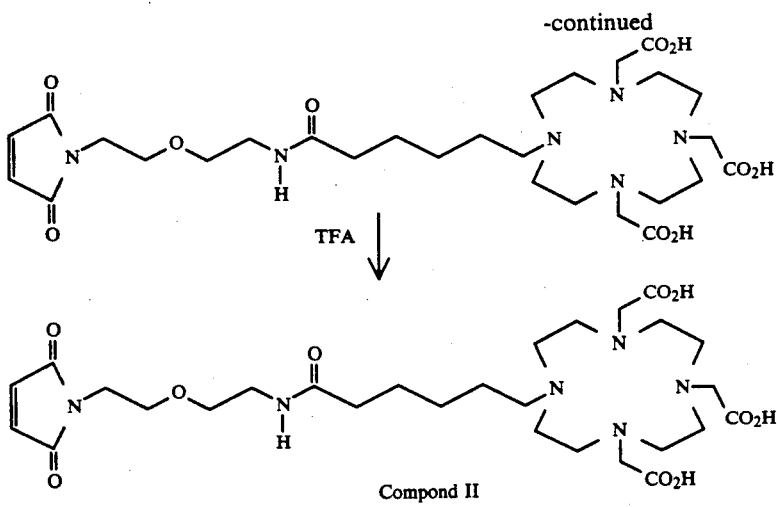

Compound II

EXAMPLES

The invention is further described in the following examples wherein all parts and percentages are by weight and all temperatures are degrees Celsius unless otherwise stated. NMR spectra are given for $^1$H at 300 MHz using TMS as an internal standard.

EXAMPLE I

Preparation of 1-(6-(5-maleimido-3-oxa-pentyloxy) 6-oxo-hexyl)-1,4,7,10-tetraazacyclododecane-4,7,10-triacetic acid (Compound I)

a) Preparation of benzyl 6-bromohexanoate.

A solution of 6-bromohexanoic acid (31.9 g, 164 mmoles) and benzyl alcohol (19.4 g, 180 mmoles) in $CH_2Cl_2$ (400 mL) was treated with dicyclohexylcarbodiimide (37 g, 180 mmoles) followed by 4-dimethylaminopyridine (2.2 g, 18 mmoles). After stirring for 5 hours the precipitated urea was removed by filtration and the filtrate was concentrated under reduced pressure. Upon kugelrohr distillation of the residue, the bromo ester (31.5 g, 68%) was collected between 110° and 120° C. at 1.5 mmHg. NMR ($CDCl_3$) $\delta$1.52 (m, 2H), 1.73 (m, 2H), 1.93 (m, 2H), 2.45 (t, 2H), 3.44 (t, 2H), 5.21 (s, 2H), 7.42 (s, 5H).

b) Preparation of 1-(6-benzyloxy-6-oxohexyl)-1,4,7,10-tetraazacyclododecane.

A solution of benzyl 6-bromohexanoate (1.1 g, 3.8 mmoles) and 1, 4, 7, 10-tetraazacyclododecane (1.3 g, 7.5 mmoles, Richman, J. E. and Atkins, T. J., J. Am. Chem. Soc., 96, 2268 (1974)) in acetonitrile (80 mL) was refluxed for 30 minutes. The solvent was removed under reduced pressure and the residue was taken up in $CH_2Cl_2$, washed twice with water, and dried over $NaSO_4$. Removal of the solvent gave the mono alkylated amine as an oil (1.26 g, 88%). NMR ($CDCl_3$) $\delta$1.36 (m, 2H), 1.48 (m, 2H), 1.65 (m, 2H), 2.40 (m, 4H), 2.63 (m, 12H), 2.81 (m, 4H), 5.18 (s, 2H), 7.41 (s, 5H).

c) Preparation of 1-(6-benzyloxy-6-oxohexyl)-1,4,7,10-tri-(tert-butoxy-2-oxoethyl)-1,4,7,10-tetraazacyclododecane.

To the above monoalkyl amine (1.26 g, 3.3 mmoles) in acetonitrile (40 mL) was added tert-butyl bromoacetate (2.5 g, 13 mmoles) and diisopropylethylamine (1.9 g, 15 mmole). The solution was refluxed for 1 hour and the solvent was removed. The residue was taken up in $CH_2Cl_2$, washed with water, aq. $NaHCO_3$, and dried ($Na_2SO_4$). Removal of the solvent gave an oil which was chromatographed ($SiO_2$, $CH_2Cl_2$—$CH_3OH$ gradient) to give the tetraalkylated product as a glass (1.7 g, 72%). NMR ($CDCl_3$) $\delta$ 1.41 (s, 27H), 1.59 (m, 6H), 2.33 (m, 8H), 2.72 (m, 4H), 2.89 (m, 4H), 3.05 (m, 4H), 3.21 (m, 4H), 3.41 (s, 2H), 5.08 (s, 2H, 7.35 (s, 5H).

d) Preparation of 1-(5-carboxypentyl)-4,7,10-(tri-tert-butoxy-2-oxoethyl)-1,4,7,10-tetraazacyclododecane.

The benzyl ester described above (0.9 g, 1.4 mmoles) was dissolved in $CH_{30}H$ (30 mL). Pd/C catalyst (0.2 g of 5%) was added and the mixture was hydrogenated on a Parr apparatus at 45 psig for 1 hour. The catalyst was removed by filtration through celite and the filtrate was concentrated under reduced pressure to an oil. The residue was chromatographed ($SiO_2$, $CH_2Cl_2$—$CH_3OH$ gradient) to provide the acid (0.28 g, 36%) as a glass. NMR ($CDCl_3$) $\delta$ 1.51 (m, 33H), 2.42 (m, 10H), 2.80 (m, 10H), 3.18 (m, 6H).

e) Preparation of 2-(2-maleimidoethoxy)ethanol.

A solution of 2-(2-aminoethoxy)ethanol (1.35 g, 13 mmoles) in saturated $NaHCO_3$ (65 mL) was cooled in an ice bath and treated with N-methoxycarbonylmaleimide (2.00 g, 13 mmoles). After 20 minutes, the ice bath was removed and the solution was extracted with $CHCl_3$ (3—50 mL) and the combined extracts were dried ($Na_2SO_4$) Removal of the solvent under reduced pressure gave the maleimido alcohol as an oil (1.70 g, 71%). NMR ($CDCl_3$) $\delta$ 2.32 (t, 1H, —OH), 3.54 (m, 2H), 2.64 (m, 6H), 6.72 (s, 2H).

f) Preparation of 1-(6-(5-maleimido 3-oxapentyloxy)-6-oxohexyl-4,7,10-tri-(tert-butoxy-2-oxoethyl)-1,4,7,10-tetraazacyclododecane.

A solution of the monoacid tri-(tert-butyl ester) described above (0.60 g, 0.95 mmoles) and 2-(2-maleimidoethyoxy)ethanol (0.20 g, 1.1 mmoles) in $CH_2Cl_2$ (10 mL) was treated with dicyclohexylcarbodiimide (0.22 g, 1.0 mmoles) and 4-dimethylaminopyridine (0.02 g, 0.16 mmoles). After stirring for 2.5 hours the mixture was filtered and the filtrate was concentrated and chromatographed ($SiO_2$, $CH_2Cl_2$—$CH_3OH$ gradient) to yield the maleimido ester (0.24 g, 32%) as a glass. NMR ($CDCl_3$) $\delta$ 1.50 (m, 33H), 2.38 (m, 12H), 2.87 (bm, 8H), 3.17 (m, 6H), 3.71 (m, 4H), 3.78 (m, 2H), 4.21 (m, 2H), 6.79 (s, 2H).

g) Preparation of 1-(6-(5-maleimido-3-oxapentyloxy)-6-oxohexyl)-1,4,7,10-tetraazacyclododecane-4,7,10-triacetic acid (Compound I).

The above tert-butyl ester (0.20 g, 0.25 mmoles) was stirred in trifluoroacetic acid (2 mL) for 1 hour. The trifluoroacetic acid was removed under vacuum and residual acid was chased by taking the residue up in acetonitrile followed by removal the solvent under vacuum. Compound I was obtained as a glass (0.14 g, 90%) after drying under vacuum. NMR (D$_2$O) δ 1.38 (m, 6H), 1.62 (m, 2H), 1.79 (m, 4H), 2.38 (m, 2H), 3.12 (m, 8H), 3.26 (m, 2H), 3.52 (m, 8H), 3.73 (m, 4H), 4.18 (m, 4H), 6.86 (s, 2H).

EXAMPLE II

Preparation of 1-(6-oxo-7-aza-10-oxa-12-(1-maleimido) dodeyl)-1,4,7,10-tetraazacyclododecane-4,7,10-triacetic acid (Compound II)

a) Preparation of tert-butyloxycarboxyaminoethyl cyanomethyl ether.

A solution of N-t-BOC-ethanolamine (12.9 g, 80 mmoles) in THF (400 mL) under Ar was cooled in an ice bath and treated dropwise with a solution of sodium bis(trimethylsilyl)amide (85 mL of 1 M in THF, 85 mmoles) with mechanical stirring. Upon completion of the addition, the mixture was stirred an additional 15 minutes and treated dropwise with bromoacetonitrile (9.6 g, 80 mmoles) in THF (50 mL). After warming to room temperature, the solvent was removed under reduced pressure and the residue was taken up in ethyl acetate and washed several times with water. The organic phase was dried (Na$_2$SO$_4$) and removal of the solvent gave an oil which was chromatographed (SiO$_2$, hexanes-ethyl acetate gradient) to afford the nitrile ether (5.3 g, 33%) as an oil. NMR (CDCl$_3$) δ 1.54 (s, 9H), 3.42 (t, 2H), 3.70 (t, 2H), 4.33 (s, 2H), 4.94 (s, 1H).

b) Preparation of 5-(tert-butyloxycarbonylamino)-3-oxa-pentyl amine.

A solution of the above nitrile (3.9 g, 19.5 mmoles) in acetic acid (60 mL) was treated with Pd/C (0.8 g of 5%) and hydrogenated on a Parr apparatus at 45 psig for 1 hour, during which time the shaker bottle was repressurized as necessary. The catalyst was removed by filtration through celite and the majority of the acetic acid was removed under reduced pressure. The residue was taken up in water and the acidic solution was extracted twice with CH$_2$Cl$_2$, and the extracts were discarded. The aqueous solution was brought to pH 12 with 50% NaOH and extracted with CH$_2$Cl$_2$. The combined extracts were dried (Na$_2$SO$_4$) and removal of the solvent gave the amine as an oil (3.0 g, 76%). NMR (CDCl$_3$) δ 1.56 (s, 9H), 2.92 (t, 2H), 3.39 (t, 2H), 3.58 (m, 4H), 5.12 (s, 1H).

c) Preparation of N-(5-tert-butyloxycarbonylamino-3-oxa-pentyl)maleimide.

The amino ether described above (2.0 g, 10 mmoles) in sat. aq. NaHCO$_3$ (50 mL) was cooled in an ice bath. N-methoxycarbonylmaleimide (1.6 g, 10 mmoles) was added in 1 portion. After stirring 30 minutes, the ice bath was removed and stirring was continued for an additional 30 minutes. The aqueous mixture was extracted with CH$_2$Cl$_2$ and the combined extracts were dried (Na$_2$SO$_4$), concentrated, and chromatographed (SiO$_2$, hexanes-ethyl acetate) to yield the maleimide (1.7 g, 60%). NMR (CDCl$_3$) δ 1.53 (s, 9H), 3.28 (m, 2H), 3.53 (t, 2H), 3.62 (t, 2H), 3.75 (m, 2H), 4.95 (s, 1H), 6.72 (s, 2H).

d) Preparation of N-(5-amino-3-oxapentyl)maleimide trifluoroacetate.

The N-tBOC derivative described above (1.6 g, 5.6 mmoles) was stirred in TFA (10 mL) for I hour. Excess TFA was removed under vacuum to give the amine salt as an oil which crystallized from ether (1.5 g, 90%). NMR (DMSO-d$_6$) δ 2.94 (m, 2H), 3.60 (m, 6H), 7.07 (s, 2H).

e) Preparation of 1-(6-(N-hydroxysuccinimidyl)-6-oxohexyl)-4,7,10-tri-(tert-butoxy-2-oxoethyl)-1,4,7,10-tetraazacyclododecane.

A solution of 1-(5-carboxypentyl)-4,7,10-tri-tert-butoxycarboxymethyl-1,4,7,10-tetraazacyclododecane (0.3 g, 0.48 mmoles), N-hydroxysuccinimide (0.06 g, 0.52 mmoles) and dicyclohexylcarbodiimide (0.11 g, 0.53 mmoles) in THF (6 mL) was stirred overnight. The mixture was filtered and the solvent removed to provide the NHS ester (0.3 g, 85%) suitable for use in the following procedure.

f) Preparation of 1-(6-oxo-7-aza-10-oxa-12-(1-maleimido)dodecyl)-4,7,10-tri-(tert-butoxy-2-oxoethyl)-1,4,7,10-tetraazacyclododecane.

A solution of the above NHS ester (0.3 g, 0.4 mmoles) and N-(5-amino-3-oxa-pentyl)maleimide trifluoroacetate (0.14 g, 0.5 mmoles) was treated with diisopropylethyl amine (80 μl, 0.5 mmoles) and stirred for 3 hours. The mixture was filtered, concentrated and chromatographed (SiO$_2$, CH$_2$Cl$_2$—CH$_3$OH gradient) to give the amide (0.09 g, 29%) as a glass. NMR (CDCl$_3$) δ 1.53 (s, 33H), 2.38 (m, 12H), 2.80 (m, 6H), 3.06 (m, 4H), 3.19 (m, 2H), 3.38 (m, 4H), 3.56 (m, 2H), 3.63 (m, 2H), 3.74 (m, 2H), 6.79 (s, 2H).

g) Preparation of 1-(6-oxo-7-aza-10-oxa-12-(1-maleimido)dodecyl -1, 4, 7, 10-tetraazacyclododecane-1,4,7,10-triacetic acid (Compound II).

The above tri-(tert-butyl ester) (0.9 g, 0.1 mmol) was stirred in trifluoroacetic acid (1 mL) for 1 hour. The trifluoroacetic acid was removed under vacuum and residual acid was removed by taking the residue up in CH$_2$Cl$_2$ followed by removal of the solvent. Compound II was obtained as a glass after drying under vacuum (0.06 g, 85%). NMR (D$_2$O) δ 1.44 (m, 6H), 1.60 (m, 6H), 1.75 (m, 2H), 2.21 (m, 2H), 3.11 (m, 6H), 3.26 (m, 2H), 3.38 (m, 4H), 3.53 (m, 8H), 3.64 (m, 6H), 4.20 (m, 2H), 6.82 (s, 2H).

EXAMPLE III

Coupling of 1-(6-(5-maleimido-3-oxa-pentyloxy)-6-oxahexyl)-1, 4, 7, 10- tetraazacyclododecane -4, 7, 10- triacetic acid (Compound I) to Antimyosin Antimyosin Fab' (1 mL, 2.5 mg) pH 7.2 in 10 mM phosphate containing 0.15 M NaCl was analyzed for sulfhydryl content. An aliquot (50 μL) was removed and diluted to 1.0 mL with 0.01 M phosphate pH 8.0. To this was added 50 μL of 5 mg/mL 5,5'dithiobis(2-nitrobenzoic acid) (DTNB, Ellman's reagent) in 0.10 M phosphate pH 8.0. The solution was mixed and the A$_{412}$ measured after 15 minutes. Equivalents of sulfhydryls were determined from a molar absorption coefficient of 15,800 at 412 nm and a protein MW of 50,000. A value of 2.7 sulfhydryl/mole was determined. The remaining Antimyosin solution (900 μL) was treated with 20 μL of 4.9 mg/80 μL Compound I in DMF. The solution was mixed and allowed to stand at room temperature for 1.5 hours. The reaction mixture was purified by Sephadex G-25 (medium) chromatography (1×10 cm), eluting with 10 mM phosphate, pH 7.2, containing 0.15 M NaCl. Fractions (1 mL) were collected and analyzed for protein concentration by A$_{280}$. Aliquots (50 μL) of the protein containing fractions were diluted to 1.0 mL with 0.01 M phosphate, pH 8.0, and treated with DTNB as above. No absorption was found at 412 nm. Fraction 5 had $A_{280}=1.58$ and fraction 6 had $A_{280}=1.44$. The conjugate was further purified by HPLC (DuPont GF250 column) eluting with 0.2 M sodium phosphate buffer, pH 6.8. The protein containing fractions were concentrated (Centricon-10) and the buffer was exchanged to 10 mM sodium phosphate, 0.15 M NaCl. The final protein-conjugate concentration was 1 mg/mL.

EXAMPLE IV

Indium-111 Labeling of Antimyosin Modified with Compound I

A sample of Antimyosin-Compound I conjugate (100 μL of 1 mg/mL) was removed with an acid-washed metal-free pipet tip and placed in an acid-washed metal-free 1.5 mL miorofuge tube. To this was added 100 μL of 0.2 M citrate, pH 5.0 using an acid-washed metal-free pipet tip, and the solution was allowed to incubate at room temperature for 15 minutes. To the acidified protein was added indium-111 chloride (50 μL, 0.35 mCi). After 30 minutes, HPLC showed 100% of the radioactivity at $R_t$ 9.5 (Fab').

What is claimed is:

1. A coupling agent of the formulas

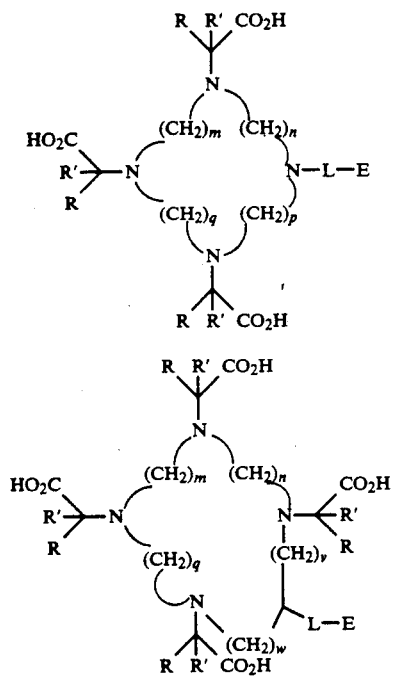

wherein E is a group capable of reacting with a site on a protein; L is an organic linking radical which may contain a cleavable site; R and R' are independently hydrogen or lower alkyl; m, n, p and q are integers which are independently selected from the group consisting of 2 and 3; v and w are integers which are independently selected the group consisting of 0, 1, and 2.

2. The coupling agent of claim 1 wherein E is a sulfhydryl selective electrophile.

3. The coupling agent of claim 2 wherein E is selected from the group consisting of haloalkyl, sulfonate ester, maleimide and aziridine.

4. The coupling agent of claim 3 wherein E is selected from the group consisting of $ClCH_2CONH$—, $BrCH_2CONH$—, $ICH_2CONH$—, and N-substituted maleimide.

5. The coupling agent of claim 1 wherein L is selected from the group consisting of optionally substituted alkyl, optionally substituted alkyl containing heteroatom substituents for carbon, and optionally substituted aryl groups.

6. The coupling agent of claim 5 where L contains at least one cleavable site.

7. The coupling agent of claim 6 wherein L is selected from those of the formula:

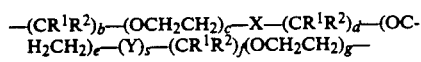

wherein each $R^1$ and $R^2$ is independently selected from the group consisting of hydrogen, lower alkyl, carboxyl, hydroxyalkyl and alkoxyalkyl; b is an integer of from 0 to 12 inclusive, c is an integer of from 0 to 5 inclusive, X is selected from the group consisting of —COO—, —CONR³— or —COS—, —OCH₂COO—, —OOC—, —R³NOC—, —SOC—, —OOCCH₂O—, —OAr— and —ArO—; Ar represents an aromatic moiety; R³ is hydrogen or lower alkyl; d, e, f and g are independently integers from 0 to 5 inclusive; s is 0 or 1; Y is selected from the same group as X, provided that when X is —CONR³— or —R³NOC—, then s is 1 and Y is —COO—, —COS—, —OCH₂COO—, —OOC—, —SOC—, —OOCCH₂O—, —OAr— or —ArO—.

8. The bifunctional coupling agent of claim 7 wherein L has the formula —$(CH_2)_5CO_2CH_2CH_2OCH_2CH_2$—.

9. The bifunctional coupling agent of claim 5 which has the formula

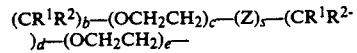

wherein each $R^1$ and $R^2$ is independently selected from the group consisting of hydrogen, lower alkyl, carboxyl, hydroxyalkyl and alkoxyalkyl; b is an integer of from 0 to 12 inclusive; c, d and e are independently integers of from 0 to 5 inclusive; Z is selected from the group consisting of —CONR₃—, —R³NOC—, and —Ar—; $R^3$ is hydrogen or lower alkyl; Ar is an aromatic moiety; and s is 0 or 1.

10. The bifunctional coupling agent of claim 9 where L is selected from the group consisting of —$(CH_2)_5CONHCH_2CH_2OCH_2CH_2$— and —$CH(CO_2H)CH_2CH_2CONHCH_2CH_2OCH_2CH_2$—.

11. The bifunctional coupling agent of claim 1 which has the formula

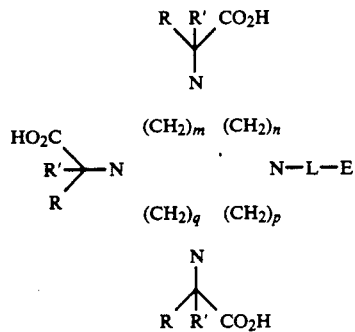

12. The bifunctional coupling agent of claim 1 which has the formula

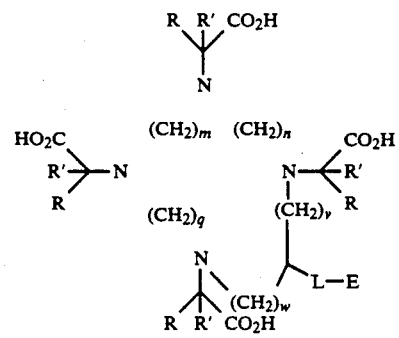

13. The bifunctional coupling agent of claim 1 wherein R and R' are H.

14. The bifunctional coupling agent of claim 11 wherein m, n, p and q are each 2.

15. The bifunctional coupling agent of claim 12 wherein m, n and q are each 2 and w is 1, and v is 0.

16. The bifunctional coupling agent of claim 7 where E is selected from the group consisting of ClCH$_2$CONH—, BrCH$_2$CONH—, ICH$_2$CONH—, and N-substituted maleimide.

17. The bifunctional coupling agent of claim 9 where E is selected from the group consisting of ClCH$_2$CONH—, BrCH$_2$CONH—, ICH$_2$CONH—, and N-substituted maleimide.

18. The bifunctional coupling agent of claim 16 where R and R' are H, and where m, n, p and q are each 2.

19. The bifunctional coupling agent of claim 16 where R and R, are each H and where m, n and q are each 2, w is 1 and v is 0.

20. The bifunctional coupling agent of claim 17 where R and R' are H, and where m, n, p and q are each 2.

21. The bifunctional coupling agent of claim 17 where R and R' are each H and where m, n and q are each 2, w is 1 and v is 0.

22. The bifunctional coupling agent of claim 1 which has the formula

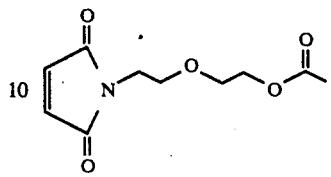

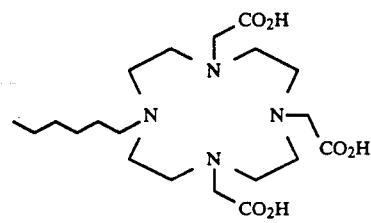

23. The bifunctional coupling agent of claim 1 which has the formula

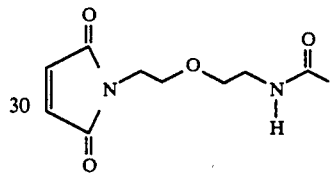

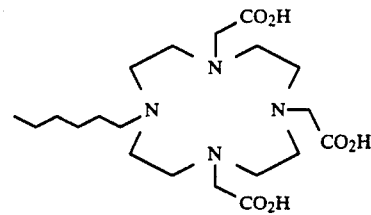

* * * * *

UNITED STATES PATENT AND TRADEMARK OFFICE
CERTIFICATE OF CORRECTION

PATENT NO. : 5,053,503
DATED : October 1, 1991
INVENTOR(S) : Richard T. Dean and Robert W. Weber It is certified that error appears in the above-identified patent and that said Letters Patent is hereby corrected as shown below:

Column 2, line 22, delete "Park" and insert therefor --Paik--.

Column 4, line 24, delete "$H_2CH_2)_e-(Y)_a-(CR^1R^2)_f(OCH_2CH_2)_g-$" and insert therefor --$H_2CH_2)_e-(Y)_a-(CR^1R^2)_f-(OCH_2CH_2)_g-$ --

Column 4, line 33, insert --aromatic-- before the word "moiety".

Column 4, line 60, insert -- - -- after "$H_2OCH_2CH_2$".

Column 14, line 29, delete "$CH_{30}H$" and insert therefor --$CH_3OH$--.

Column 14, line 43, after the words "the solution was", insert --stirred at room temperature for 30 minutes. The solution was--.

Column 14, line 44, delete "(3-50 mL)" and insert therefor -- (3 x 50 mL)--.

Column 14, line 45 insert -- . -- after "($Na_2SO_4$)".

Column 16, line 43, delete "6-oxahexyl" and insert therefor --6-oxohexyl--.

Column 18, line 43, delete "-$CONR_3$-" and insert therefor -- -$CONR^3$- --.

Column 19, line 38, delete "where R and R," and insert therefor --where R and $R^1$--.

UNITED STATES PATENT AND TRADEMARK OFFICE
CERTIFICATE OF CORRECTION

Page 2 of 5

PATENT NO. : 0,053,503
DATED : October 1, 1991
INVENTOR(S) : Richard T. Dean and Robert W. Weber It is certified that error appears in the above-identified patent and that said Letters Patent is hereby corrected as shown below:

Column 11, lines 51 - 58, delete

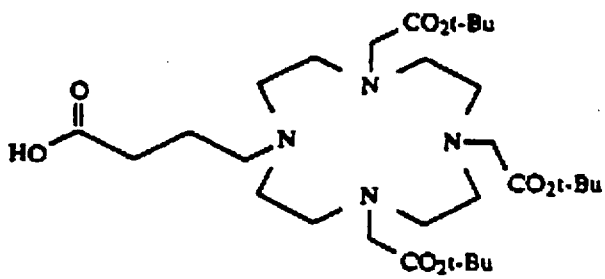

and insert therefor

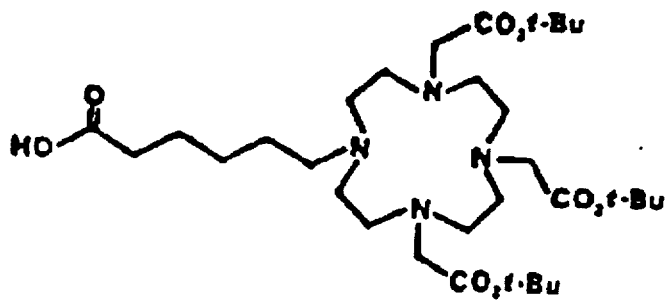

UNITED STATES PATENT AND TRADEMARK OFFICE
CERTIFICATE OF CORRECTION

PATENT NO. : 5,053,503
DATED : October 1, 1991
INVENTOR(S) : Richard T. Dean and Robert W. Weber It is certified that error appears in the above-identified patent and that said Letters Patent is hereby corrected as shown below:

Column 13, lines 1-10 delete

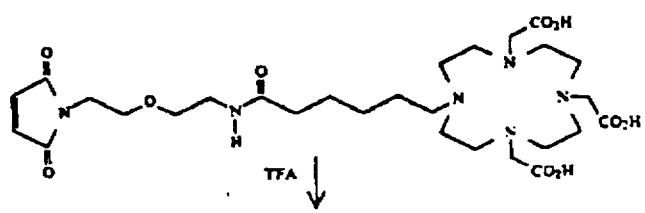

and insert therefor

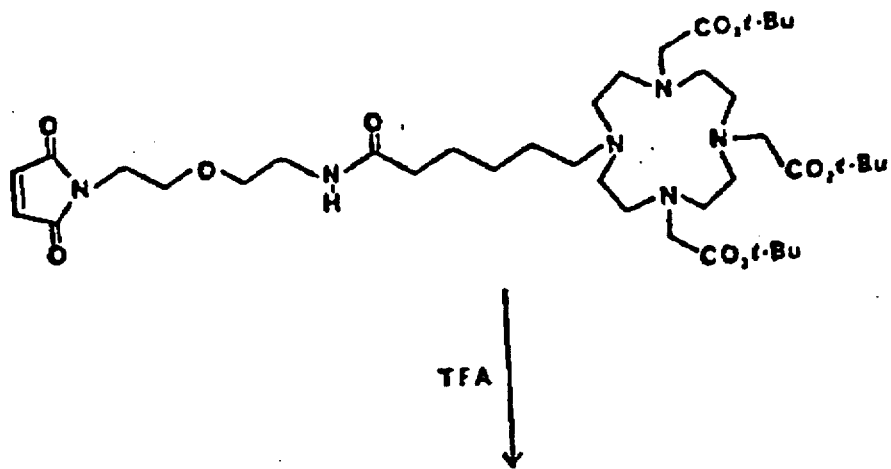

UNITED STATES PATENT AND TRADEMARK OFFICE
CERTIFICATE OF CORRECTION

PATENT NO. : 5,053,503
DATED : October 1, 1991
INVENTOR(S) : Richard T. Dean and Robert W. Weber It is certified that error appears in the above-identified patent and that said Letters Patent is hereby corrected as shown below:

Column 18, lines 52-65 delete

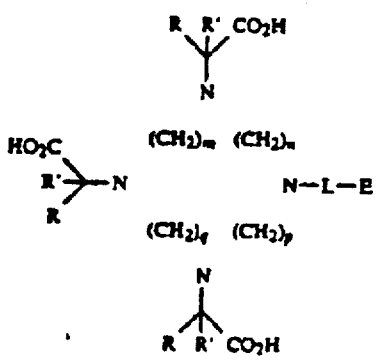

and insert therefor

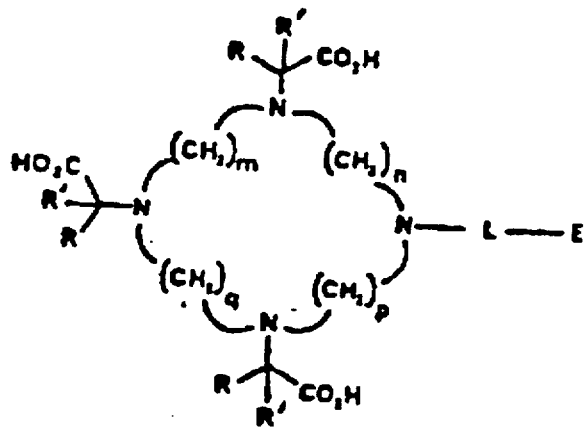

UNITED STATES PATENT AND TRADEMARK OFFICE
CERTIFICATE OF CORRECTION

PATENT NO. : 5,053,503
DATED : October 1, 1991
INVENTOR(S) : Richard T. Dean and Robert W. Weber It is certified that error appears in the above-identified patent and that said Letters Patent is hereby corrected as shown below:

Column 19, lines 1-15 delete 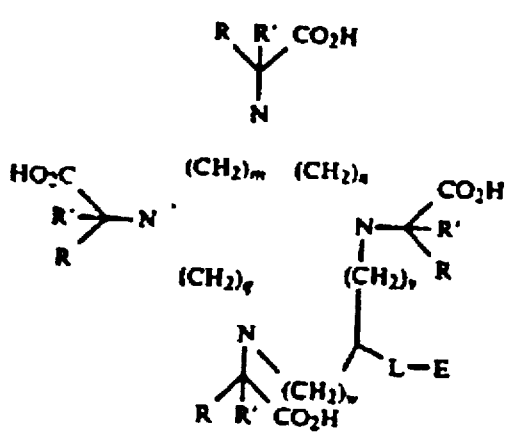 and insert therefor 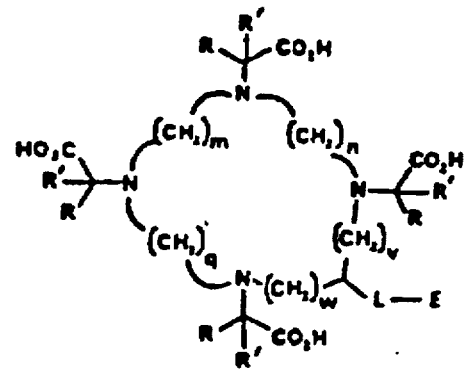

Signed and Sealed this

Nineteenth Day of October, 1993

Attest:

BRUCE LEHMAN

Attesting Officer   Commissioner of Patents and Trademarks